United States Patent [19]

Allen et al.

[11] Patent Number: 4,739,176
[45] Date of Patent: Apr. 19, 1988

[54] MONITORING FOR CONTAMINANTS IN TEXTILE PRODUCT

[75] Inventors: Lindsay A. Allen, Highton; Peter R. Lamb, Belmont; Dieter E. Plate, Torquay, all of Australia

[73] Assignee: Commonwealth Scientific and Industrial Research Organization, Australia

[21] Appl. No.: 848,009

[22] Filed: Apr. 3, 1986

[30] Foreign Application Priority Data

Apr. 4, 1985 [AU] Australia .............................. PH00022

[51] Int. Cl.⁴ .......................... G01N 21/88; G01J 3/50
[52] U.S. Cl. .................................... 250/572; 250/226; 356/430
[58] Field of Search ............... 250/571, 572, 559, 562, 250/226; 356/429, 430, 446, 431

[56] References Cited

U.S. PATENT DOCUMENTS

| | | | |
|---|---|---|---|
| 3,019,972 | 2/1962 | Strother | 250/563 |
| 3,044,345 | 7/1962 | Schottler | 356/430 |
| 3,116,621 | 1/1964 | Klein et al. | 250/562 |
| 3,264,922 | 7/1966 | Peyer | 356/386 |
| 3,451,756 | 6/1969 | Young | 250/561 |
| 3,971,272 | 7/1976 | Felix | 28/227 |
| 4,011,457 | 3/1977 | Wolf | 356/431 |
| 4,634,280 | 1/1987 | Paulson, Jr. | 250/571 |

FOREIGN PATENT DOCUMENTS 933331  4/1948  France .
1411254 10/1975 United Kingdom .
2095828 10/1982 United Kingdom .

OTHER PUBLICATIONS

"Dark Fibres and Their Economic Importance", Foulds et al., *Wool Technology and Sheep Breeding*, Jun.-/Jul., 1984.

Primary Examiner—David C. Nelms
Assistant Examiner—Michael Messinger
Attorney, Agent, or Firm—Sughrue, Mion, Zinn, Macpeak, and Seas

[57] ABSTRACT

A method of monitoring for contaminants in highly elongate textile product such as yarn includes diffusely applying light to the yarn and monitoring light reflected by the yarn. The yarn is drawn past a background therefor and light is diffusely applied to both the yarn and said background. The background is arranged so that the total amount of monitored light reflected from the yarn and the background is substantially independent of the dimensions and density of the yarn and of the distribution of constituents in the yarn. In this way, a prescribed change in the reflected light intensity indicates a selected contaminant or range of contaminants in the yarn. The background is conveniently provided by an elongate channel so as to be close behind and to each side of the yarn.

15 Claims, 5 Drawing Sheets

MONITORING FOR CONTAMINANTS IN TEXTILE PRODUCT

This invention relates to the detection of contaminants in highly elongate textile product such as yarn and is especially but not exclusively concerned with the detection and removal of vegetable matter from wool yarn.

The retention of vegetable matter in the final fabric remains a significant problem in the processing of wool. Most of the vegetable matter present in raw wool is normally removed during the succession of normal wool processing steps including carding, combing, spinning and winding, but a small proportion does reach the final fabric. This residual vegetable matter is generally removed manually during mending, a very expensive operation whose cost relative to other steps in the processing sequence is steadily rising. Fabric manufacturers are therefore applying increasingly stringent limits on the acceptable level of such faults in yarns. Because the vegetable matter, which may typically be a burr or very small twig, is frequently interlocked into a woven or knitted fabric, repair of the fabric is at time also required.

It is known to remove vegetable matter from fabrics by carbonising, using acid and heat. This is, however, a costly operation which generally causes some damage to the wool-fibre resulting in reduced wear life. Carbonising also places limitations on the types of fabric-dyes and the types of blend-fibres that can be used.

It is also known to monitor changes in yarn diameter by detecting light which passes or is reflected by a travelling yarn. Examples of such arrangements are disclosed in British Pat. No. 2,064,106 and U.S. Pat. Nos. 3,264,922, 3,712,743, 3,907,440, 3,945,181 and 4,091,368. These approaches generally rely upon changes in the proportion of light passed or reflected when the diameter of the yarn varies and clearly have no useful application to the detection of contaminants such as vegetable matter as the presence of contaminants will not necessarily be reflected in corresponding changes in apparent yarn diameter.

In a quite different field, there have been disclosures of techniques for sorting discrete objects on the basis of colour-based changes in reflected light. These disclosures include published British patent application Nos. 2,133,535 and 2,136,957, and U.S. Pat. No. 3,914,601. In British patent application No. 2,136,957, for exmaple, grains or other granular objects fall through a spacious chamber in which they are diffusely illuminated by multiple lamps. Photodetectors are arranged to receive light of a substantially constant amount independent of the quantity of normal or acceptable grain in the sorting path, but the appearance of any grains of different colour will cause a detectable change in the reflected light received at the detectors. It is considered, however, that the spacious chamber (which is also a feature of U.S. Pat. No. 3,914,601) is not simply adaptable to yarns—a product very different from grains—since the location of the yarn components and thus of the contaminants is not uniform and since the spacing of the contaminants and of other yarn faults and variations cannot be adequately controlled to minimise shadows cast by one localised yarn feature on another, for example, by loosely bound neps and slubs. The chamber will also tend to fill with fly and the like, further affecting readings.

It is an object of the invention to provide a method and apparatus for monitoring for selected contaminants in highly elongate textile product, and in particular to provide a method and apparatus for monitoring for vegetable matter in wool yarn.

The invention accordingly provides a method of monitoring for contaminants in highly elongate textile product such as yarn comprising diffusely applying light to the product and monitoring the light reflected by the product, characterized in that:
  the textile product is drawn past a background therefor, in that
  light is diffusely applied to both the product and said background, and in that
  the background is arranged so that the total amount of light reflected from the textile product and the background is substantially independent of the dimensions and density of the product and of the distribution of constituents in the product,
  whereby a prescribed change in the reflected light intensity indicates a selected contaminant or range of contaminants in the textile product.

Preferably, said textile product is drawn through an elongate channel so that the channel defines said background close behind and to each side of the product.

The background is preferably arranged to be of reflectivity similar to the textile product, e.g. of a colour apparently similar to the textile product when illuminated by said light.

The light is preferably diffusely applied by diffusely illuminating the textile product from each of at least two directions.

In addition or alternatively, the background may be semi-opaque and the light applied by directing light through the background.

The textile product may be a strand, filament or yarn. Advantageously, the method further comprises severing the strand, filament or yarn before and after a detected contaminant, discarding the resultant intermediate length, and splicing the resultant ends.

The invention also provides apparatus for monitoring for contaminants in highly elongate textile product such as yarn comprising means to diffusely apply light to the product and means to monitor the light reflected by the product, characterized in that:
  there is provided structure defining a background for the product, in that
  said means to diffusely apply light is arranged to apply light to both the product and said background, and in that
  the background is arranged so that the total amount of monitored light reflected from the textile product and the background is substantially independent of the dimensions and density of the product and of the distribution of constituents in the product,
  whereby a prescribed change in the reflected light intensity indicate a selected contaminant or range of contaminants in the textile product.

Preferably, the aforesaid structure provides an elongate channel for the travelling textile product which defines said background close behind and to each side of the product.

The invention will be further described, by way of example only, by reference to the accompanying drawings, in which.

Figure 1:
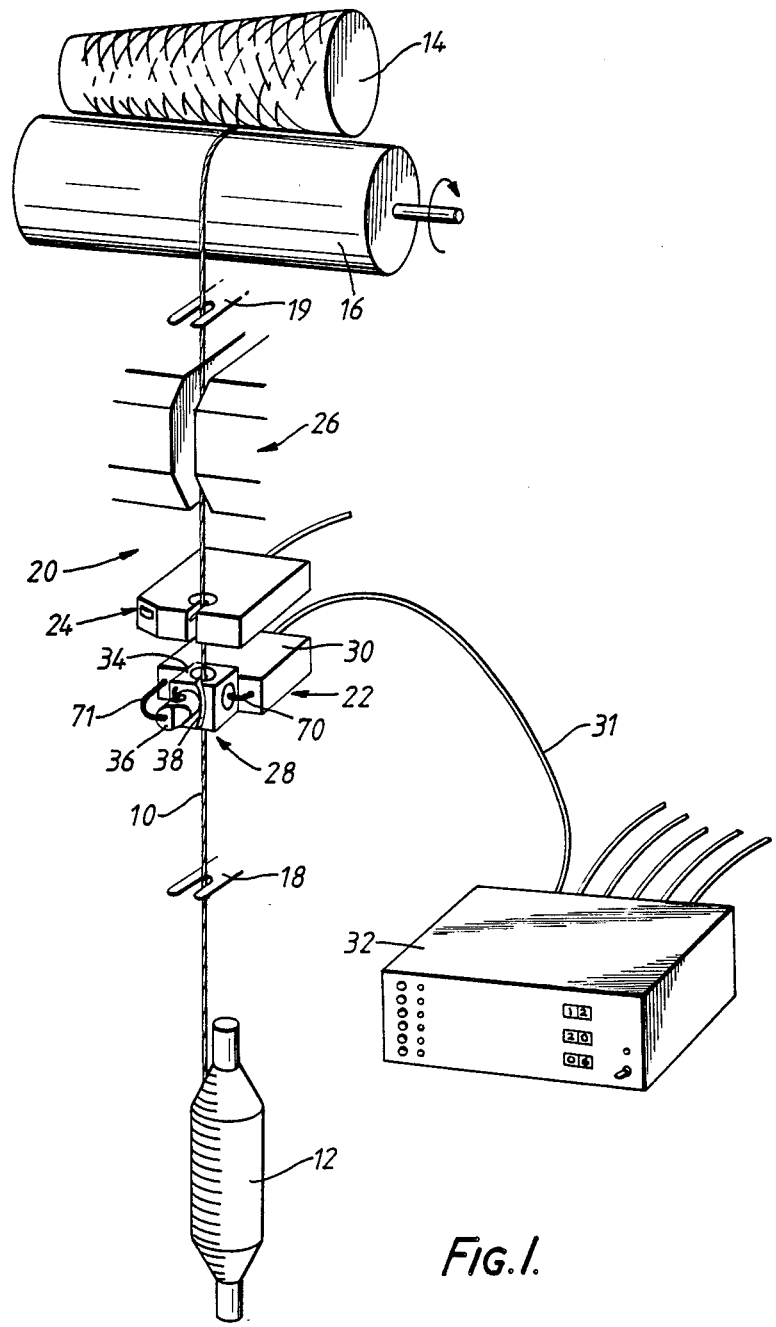
FIG. 1 is a somewhat diagrammatic front view of apparatus according to the invention shown mounted on a textile winding machine.
Figure 2:
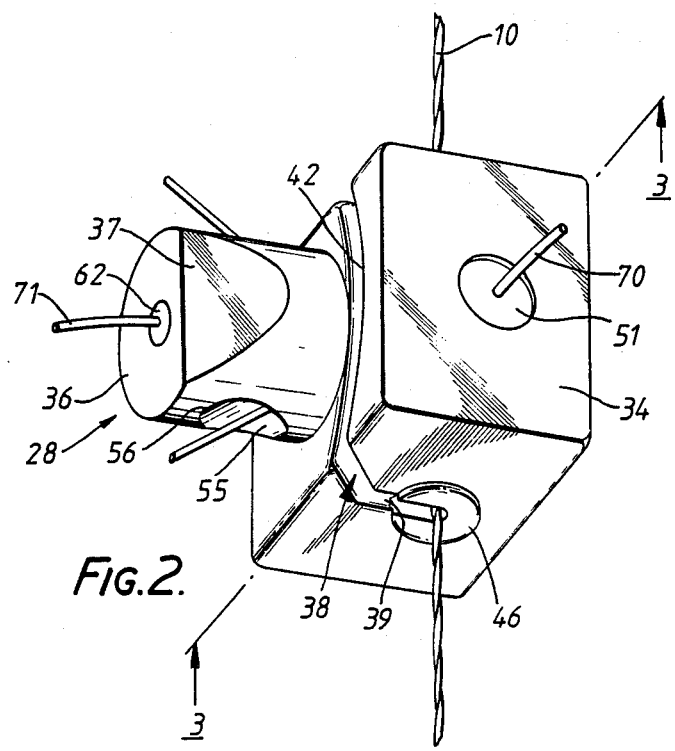
FIG. 2 is a perspective enlargement of the principal portion of the apparatus.
Figure 3:
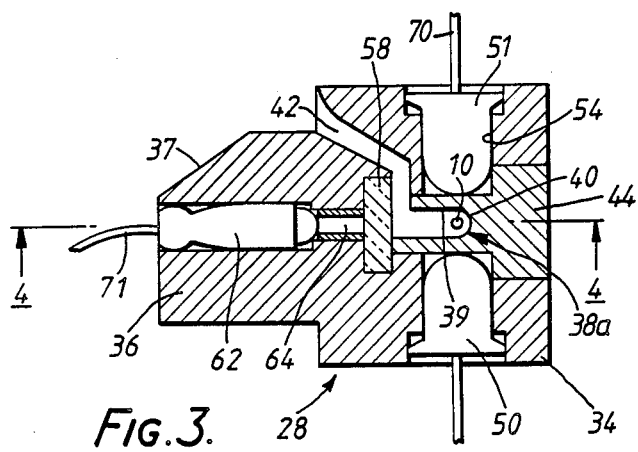
Figure 4:
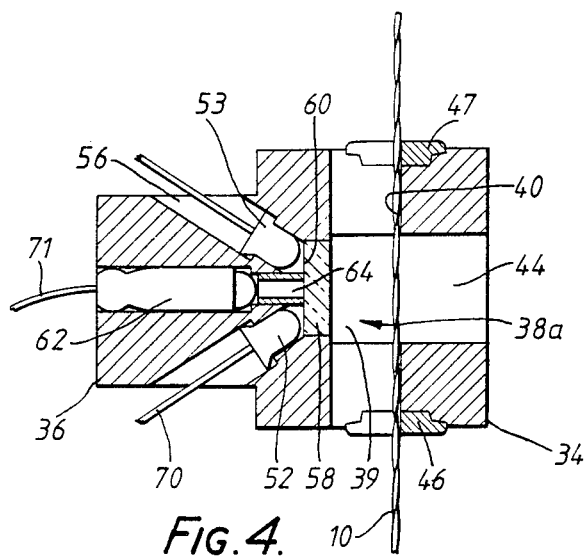
Figure 5:
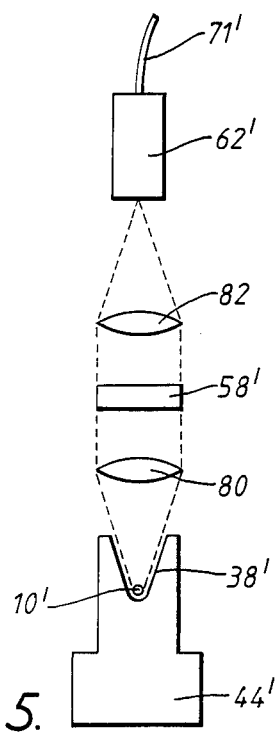

FIGS. 3 and 4 are cross-sections on the lines 3—3 and 4—4 in FIGS. 2 and 3 respectively;

FIG. 5 is a diagrammatic view of an alternative embodiment; and

Figure 6A:
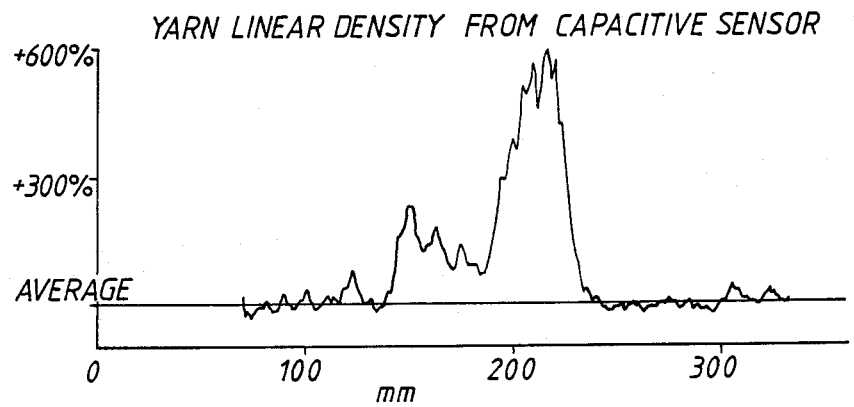
Figure 6B:
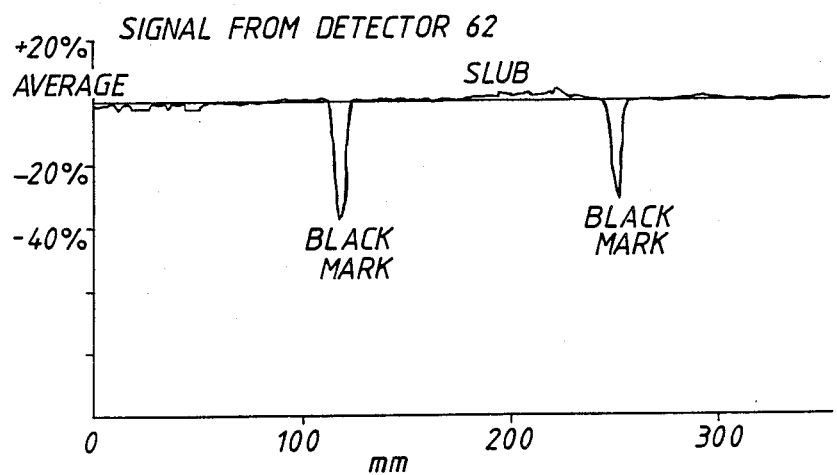
Figure 7:
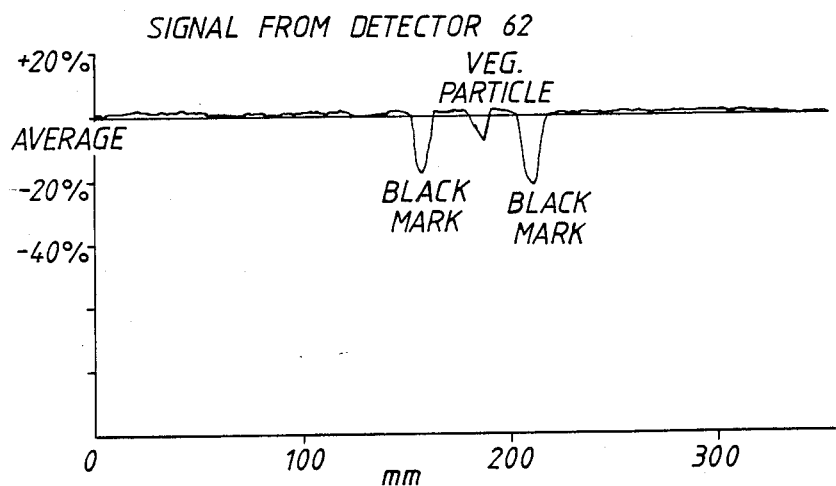
Figure 7:
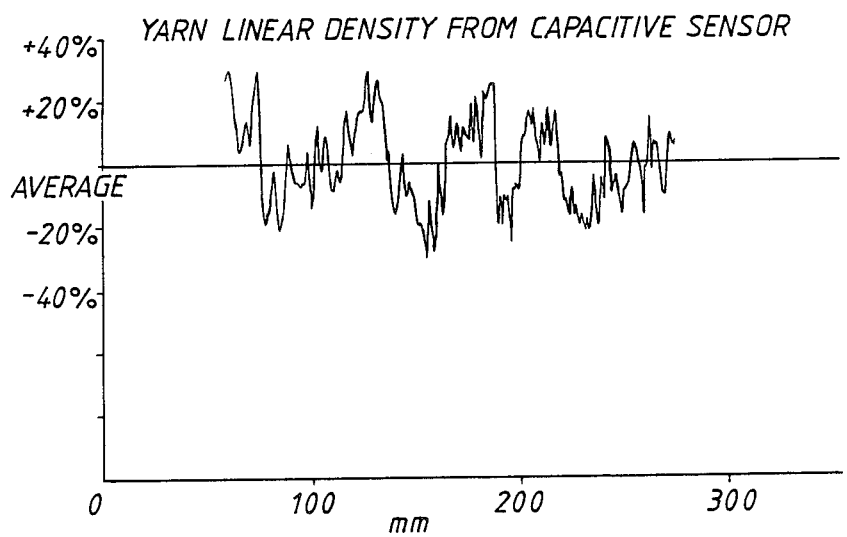

FIGS. 6A and 6B and 7 depict responses of the apparatus and of the adjacent capacitive sensor to two yarn segments respectively having black marks and a slub and black marks and a particle of vegetable matter.

In the illustrated winder, yarn 10 is drawn from a bobbin 12 onto a package 14 over a winding drum 16. Yarn 10 traverses a pair of guides 18, 19 between which is disposed fault monitoring and detection equipment generally indicated at 20. The equipment includes a vegetable and coloured matter sensor 22 comprising apparatus in accordance with the invention, a device 24 with a built-in cutter for detecting and severing off excessive variations in diameter, and a splicer or knotter 26. Detector device 24 and splicer/knotter 26 are entirely conventional but are illustrated to indicate that the sensor of the invention may typically be closely associated with these components.

Contaminant sensor 22 is illustrated in greater detail in FIGS. 2 to 4 and includes an integral head 28 supported on a mounting 30 which also houses pre-amplification and signal conditioning circuits. The circuits are coupled by a lead 31 to a controller/power supply 32.

Head 28 comprises a broadly rectangular base portion 34 and a generally tubular portion 36 outstanding from the base portion. Base portion 35 is cut to define a transversely extending channel 38 with top and bottom side faces 38 and a U-shaped floor 40. Channel 38 is open at the front of the sensor via a curved mouth 42 which extends around tubular head portion 36. As seen in FIGS. 3 and 4, the centre portion 38a of channel 38 is formed in a ceramic insert 44 which projects firmly into a complementary cavity in the base portion of the head. Each end of channel 40 is also reinforced by a respective ceramic guide 46, 47. It will be seen that yarn 10 traverses the sensor by being drawn through channel 38 and that mouth 42 provides the opening by which the yarn is introduced into the channel. This is further facilitated by truncation at 37 of the adjacent cylindrical surface of tubular head portion 36.

It will further be noted that the channel 38 provides a background 39, 40 which is close behind and to each side of the travelling yarn as it traverses the channel: as apparent from FIG. 3, the faces 39 are separated only by a distance equal to about 2 to 4 times the mean yarn diameter and the yarn is arranged by the system of guides, 18, 46, 47, 19 to pass close to the floor 40 of the channel. Proximity to a real background helps in preventing problems which would otherwise arise from shadowing by features or contaminants of the yarn. Moreover, channel 38 assists in aligning any contaminant such as a twig or the like, is substantially self-cleaning, e.g. to keep it free of fly or the like, and improves the uniformity and diffuseness of the illumination to be described below.

For the purpose of diffusely illuminating the yarn and the aforesaid background as the yarn traverses the centre portion 38a of channel 38 within ceramic insert 44, insert 44 is fashioned in a semi-opaque material and four lamps 50, 51, and 53, 53 are replaceably fitted within the body of sensor head 28. All lamps are of a type providing an apparent extended source. Lamps 50, 51 are mounted in opposite ends of a horizontal bore 54 in head base portion 34 so as to lie symmetrically with respect to yarn 10 to either side of insert 44. Lamps 52, 53 are retained in respective inclined passages 56 which are separated from channel 38 by an optical filter 58 and an annular diffuser 60. The lamps are sealed in place if necessary by suitable plugs 55. Mounted in the axial bore of tubular portion 36 of head 28 is a conventional photodetector 62: its sensitive head is aligned with channel 40 and yarn 10 so that the light path traverses filter 58 and an elongate aperture 64. Various leads, such as 70, 71, couple the four lamps and the photodetector to the circuit housed in mount 30.

The use of multiple extended light sources, filter 58 and diffuser 60, and the positioning of lamps 50, 51 behind the semi-opaque insert 44 optimise the diffuseness of the illumination and so minimise shadowing effects within the observation region of the photodetector.

When lamps 50, 53 are activated as yarn 10 is drawn through channel 38, light is diffusely applied to both the yarn and the closely proximate background 39, 40. In accordance with the invention, the material of insert 44 is selected to provide a background whereby the total amount of light reflected from the yarn and the background in any given direction, and in particular to detector 62, is substantially independent of the dimensions and density of the yarn and of the distribution of fibres in the yarn. This is achieved by providing for the reflectivity of the background to be similar to the yarn and in this case, where the yarn is a bundle of wool fibres, for the background to be of a colour apparently similar to the yarn when illuminated by the light: a substantially white background is therefore required. Thus, the signal received at controller 32 from detector 62, which is sensitive to a specific solid angle of reflected light, will not substantially vary as slubs or neps in the yarn pass through under the detector. On the other hand, any contaminant such as a black mark or piece of vegetable matter carried by the yarn will materially affect the reflectivity of that segment of the yarn and there will be a meaningful change in the signal output by detector 62. This change is used to activate the cutter in device 24 to sever the yarn adjacent the detected contaminant. The resultant yarn ends are spliced by splicer 26 so as to discard an intermediate length containing the contaminant.

FIGS. 6 and 7 demonstrate the utility of sensor 22. FIG. 6A indicates the instantaneous linear density of a yarn segment passed along channel 38 as measured by a capacitive sensor mounted locally for the prupose: it will be seen that the yarn segment includes a substantial slub. The yarn segment also carries two black marks and FIG. 6B shows the response of the photodetector 62 to the same yarn segment as it passes through sensor 22. The slub causes substantially little alteration to the base signal but two very distinctive peaks, about 30 and 40% of the base signal, are received and thereby clearly indicate the black marks.

FIG. 7 similarly shows the response of a capacitive sensor and of sensor 22 to another yarn segment which is of somewhat more random density variation but which carries a particle of vegetable matter as well as two black marks. Despite the density fluctuation, the signal from photodetector 62 is substantially constant except for clear peaks marking the presence of the black marks and the particle of vegetable matter.

It will be appreciated from FIGS. 6 and 7 that a relatively low threshold can be applied to eliminate fluctuations in the base signal, that a prescribed change in the reflected light intensity (i.e. greater than the threshold) then indicates a contaminant or range of contaminants in the yarn. The threshold may be set so that the electronics react only to a contaminant, e.g. a piece of vegetable matter, of an approximate minimum size.

It is found that vegetable matter has a lower reflectivity in blue than wool fibre to the extent that the difference in reflectivity is enhanced in blue compared to red. On the other hand, most readily available lamps and detectors have a response characteristic which peaks in the red but is quite diminished in the blue. A compromise to obtain both reasonable discrimination and an adequate signal is to filter out red in the incident light and indeed it is found that discrimination is adequate for the wave band 350 to 600 nm and that a good working range for the incident light from the four lamps is 500 to 600 nm.

FIG. 5 schematically depicts an alternative detection arrangement in conjunction with a V-section channel or groove 38' providing a close background for yarn 10'. Several extended light sources (not illustrated) illuminate the yarn and background and a segment of reflected light is directed to photodetector 62' through lens 80, filter 58' and a second lens 82.

Although this specification has primarily discussed monitoring for vegetable matter in wool yarns, the technique of the invention has other useful applications such as the detection of bale twine fibres in wool or polypropylene strands in cotton.

We claim:

1. Apparatus for monitoring for contaminants in highly elongate textile product such as yarn, comprising:
    structure defining a background for the product; and
    means to monitor the light reflected by the product and arising from the background;
    wherein said structure includes spaced side faces and a floor which define an elongate passageway for the textile product and thereby provide said background behind and to each side of the product; and
    wherein there is provided means to apply light diffusely to both the product and said background;
    whereby said background and said textile product may be matched so that the total amount of monitored light reflected from the textile product and arising from the background is substantially independent of the dimensions and density of the product and of the distribution of constituents in the product;
    a prescribed change in the intensity of the monitored reflected ight thereby indicating a selected contaminant or range of contaminants in the textile product.

2. Apparatus according to claim 1 wherein said structure provides an elongate channel with a mouth by which the textile product may be introduced into the channel.

3. Apparatus according to clain 1 wherein said light applying means is such that light is applied diffusely both towards said floor and said faces and into the passageway through the side faces.

4. Apparatus according to claim 3 wherein said light applying means is such that light applied through the side faces is applied through respective semi-opaque portions of the such faces from behind the side faces.

5. Apparatus according to claim 1 wherein said structure comprises a body with a cavity therein and an elongte channel extending through said cavity, and a ceramic insert of a semi-opaque material which is disposed in said cavity and provides a center portion of said channel in front of said monitoring means, said light applying means including light sources mounted in said body to either side of said insert for applying the light through said side faces.

6. Apparatus according to claim 5 wherein said light applying means includes respective light sources to either side of said monitoring means.

7. Apparatus according to claim 1 wherein the textile product is staple yarn and the applied light belongs to the blue-green end of the visible light spectrum whereby to enhance the difference in the reflectivity of contaminants comprising vegetable matter relative to the fibres of the yarn.

8. Apparatus according to claim 1 for monitoring for selected contaminants in yarn, wherein said background is arranged to be of reflectivity substantially equal to the yarn.

9. Apparatus according to claim 1 further comprising means actuable in response to detection by said monitoring means of a contaminant in a strand, filament or yarn to sever and splice the strand, filament or yarn so as to discard a length containing the detected contaminant.

10. A method of monitoring for contaminants in highly elongate textile product such as yarn comprising:
    drawing the textile product past a background therefor, and
    monitoring light reflected by the product and arising from the background,
    wherein the background is provided behind and to each side of the product by side faces and a floor which define an elongate passageway for the product, and light i is applied diffusely to both the product and said background through the side faces,
    and wherein said background and said textile product are matched so that the total amount of monitored light reflected from the textile product and arising from the background is substantially independent of the dimensions and density of the product and of the distribution of constituents in the product,
    a prescribed change in the intensity of the monitored reflected light thereby indicating a selected contaminant or range of contaminants in the textile product.

11. A method according to claim 10 wherein the textile product is staple yarn and the applied light belongs to the blue-green end of the visible light spectrum whereby to enhance the difference in the reflectivity of vegetable matter relative to the fibres of the yarn.

12. A method according to claim 10 wherein the background is arranged to be of reflectivity substantially equal to the textile product.

13. A method according to claim 10 wherein the background is arranged to be apparently substantially the same colour as the textile product when illuminated by said diffusely applied light.

14. A method according to claim 10 further comprising severing and splicing the strand, filament or yarn so as to discard a length containing the detected contaminant.

15. A method according to claim 10 wherein said light is applied diffusely towards said floor and side faces and into the passageway through the side faces.

* * * * *